(12) United States Patent
Collin et al.

(10) Patent No.: US 11,439,512 B2
(45) Date of Patent: Sep. 13, 2022

(54) GLENOHUMERAL COMPONENT FOR A SHOULDER PROSTHESIS, AND SHOULDER PROSTHESIS COMPRISING SUCH A GLENOHUMERAL COMPONENT

(71) Applicant: Tornier, Montbonnot-Saint-Martin (FR)

(72) Inventors: Philippe Collin, Pace (FR); Pierric Deransart, Saint Martin d'uriage (FR)

(73) Assignee: TORNIER, Montbonnot-Saint-Martin (FR)

( * ) Notice: Subject to any disclaimer, the term of this patent is extended or adjusted under 35 U.S.C. 154(b) by 286 days.

(21) Appl. No.: 16/885,055

(22) Filed: May 27, 2020

(65) Prior Publication Data

US 2020/0281735 A1 Sep. 10, 2020

Related U.S. Application Data

(63) Continuation of application No. 15/828,940, filed on Dec. 1, 2017, now Pat. No. 10,695,186.

(30) Foreign Application Priority Data

Dec. 6, 2016 (EP) ..................................... 16306625

(51) Int. Cl.
*A61F 2/40* (2006.01)
*A61F 2/30* (2006.01)

(52) U.S. Cl.
CPC .............. *A61F 2/4014* (2013.01); *A61F 2/40* (2013.01); *A61F 2/4081* (2013.01);
(Continued)

(58) Field of Classification Search
CPC .................. A61F 2/4003; A61F 2/4014; A61F 2002/3483; A61F 2002/3615;
(Continued)

(56) References Cited

U.S. PATENT DOCUMENTS

| 3,916,451 A | 11/1975 | Buechel et al. | |
|---|---|---|---|
| 4,030,143 A * | 6/1977 | Elloy | A61F 2/40 623/19.12 |

(Continued)

FOREIGN PATENT DOCUMENTS

| EP | 1 649 836 | 4/2006 |
|---|---|---|
| EP | 2 382 930 | 11/2011 |

(Continued)

OTHER PUBLICATIONS

European Search Report issued in EP Application No. 16306625.1, dated May 26, 2017, in 6 pages.

*Primary Examiner* — Megan Y Wolf
(74) *Attorney, Agent, or Firm* — Duane Morris LLP

(57) ABSTRACT

The glenohumeral component of the invention comprises a first side and a second side, which are opposite each other and which, in an implanted state in which the glenohumeral component is free-floating with respect to a humerus and a glenoid of a human shoulder, are in contact respectively with an end portion of the humerus and with a glenoid component intended to be secured to the glenoid. The first side of the glenohumeral component includes a convex articular surface that is designed to articulate with a concave bone surface prepared within the end portion of the humerus. The second side of the glenohumeral component includes a concave articular surface that is designed to articulate with a convex articular surface of the glenoid component. The corresponding shoulder prosthesis is thus reversed. Moreover, the articular interface between the glenoid component, which is secured to the glenoid, and the rest of the prosthesis has double mobility, which provides a greater range of motion between the glenoid and the humerus.

6 Claims, 4 Drawing Sheets

(52) U.S. Cl.
CPC ............ *A61F 2002/30299* (2013.01); *A61F 2002/30528* (2013.01); *A61F 2002/30654* (2013.01); *A61F 2002/30662* (2013.01); *A61F 2002/30663* (2013.01); *A61F 2002/4022* (2013.01); *A61F 2002/4051* (2013.01); *A61F 2002/4085* (2013.01)

(58) Field of Classification Search
CPC ...... A61F 2002/4007; A61F 2002/4018; A61F 2002/4022; A61F 2002/4085
See application file for complete search history.

(56) References Cited

U.S. PATENT DOCUMENTS

| | | |
|---|---|---|
| 4,919,674 A | 4/1990 | Schelhas |
| 5,171,285 A | 12/1992 | Broderick |
| 6,811,569 B1 | 11/2004 | Afriat et al. |
| 7,044,974 B2 | 5/2006 | Garber et al. |
| 7,799,077 B2 | 9/2010 | Lang et al. |
| 8,308,811 B2 | 11/2012 | Newsome et al. |
| 8,814,946 B2 | 8/2014 | Steinberg |
| 10,695,186 B2 * | 6/2020 | Collin .................. A61F 2/4014 |
| 2007/0016304 A1 | 1/2007 | Chudik |
| 2007/0225822 A1 | 9/2007 | Santilli et al. |
| 2009/0062923 A1 | 3/2009 | Swanson |
| 2009/0287309 A1 | 11/2009 | Walch et al. |
| 2009/0306782 A1 | 12/2009 | Schwyzer |
| 2011/0098822 A1 | 4/2011 | Walch et al. |
| 2011/0264153 A1 * | 10/2011 | Hassler ................ A61B 17/885 606/86 R |
| 2013/0150975 A1 | 6/2013 | Iannotti et al. |
| 2015/0289985 A1 | 10/2015 | Hopkins |
| 2015/0335441 A1 | 11/2015 | Linares et al. |
| 2018/0153701 A1 | 6/2018 | Collin et al. |

FOREIGN PATENT DOCUMENTS

| | | |
|---|---|---|
| GB | 2 166 654 | 5/1986 |
| WO | WO 2017/066504 | 4/2017 |

* cited by examiner

GLENOHUMERAL COMPONENT FOR A SHOULDER PROSTHESIS, AND SHOULDER PROSTHESIS COMPRISING SUCH A GLENOHUMERAL COMPONENT

Any and all applications for which a foreign or domestic priority claim is identified in the Application Data Sheet as filed with the present application are hereby incorporated by reference under 37 C.F.R. § 1.57. U.S. patent application Ser. No. 15/828,940, filed Dec. 1, 2017, now U.S. Pat. No. 10,695,186, is hereby incorporated by reference herein in its entirety.

The present invention concerns a glenohumeral component for a shoulder prosthesis. The invention also concerns a shoulder prosthesis comprising such a glenohumeral component.

In a healthy human shoulder, the head of the humerus, which is generally ball-shaped, and the glenoid cavity of the scapula articulate with each other and form a ball-and-socket joint. Total shoulder arthroplasty is a common treatment for shoulder pain resulting from arthritis or injury and leads to replace the ball-and-socket joint by a shoulder orthopedic prosthesis.

Such a shoulder prosthesis generally includes both a glenoid implant to be fixedly implanted at the glenoid of the scapula and a humeral implant to be fixedly implanted at the head of the humerus, the glenoid implant and the humeral implant being designed to articulate directly with each other.

The invention focuses on another type of shoulder prosthesis, in which the humeral implant to be fixedly secured to the humerus is replaced with a free-floating glenohumeral component, as proposed in US 2011/0098822. As this free-floating glenohumeral component freely articulates with a concave bone surface that is prepared within an end portion of the humerus, US 2011/0098822 describes the glenohumeral component as corresponding to an interpositional implant which has necessarily a sphere or ball shape so as to freely revolve on itself between the aforesaid concave bone surface and either a concave prosthetic surface of a glenoid component or a concave bone surface of the glenoid.

One of the goals of the present invention is to propose an improved glenohumeral component that in particular is not limited to a spherical shape.

To this end, one object of the invention is a glenohumeral component for a shoulder prosthesis, comprising a first side and a second side, which are opposite each other and which, in an implanted state in which the glenohumeral component is free-floating with respect to a humerus and a glenoid of a human shoulder, are in contact respectively with an end portion of the humerus and with a glenoid component intended to be secured to the glenoid, wherein the first side of the glenohumeral component includes a convex articular surface that is designed to articulate with a concave bone surface prepared within the end portion of the humerus, characterized in that the second side of the glenohumeral component includes a concave articular surface that is designed to articulate with a convex articular surface of the glenoid component.

Another object of the invention is a shoulder prosthesis, comprising:
 a glenohumeral component as defined above, and
 a glenoid component, which is designed to be secured to a human glenoid and which has a convex articular surface with which the concave articular surface of the glenohumeral component articulates.

Thanks to the invention, the shoulder prosthesis is reversed, in the sense that the natural anatomy of the ball-and-socket joint of the shoulder is reversed. In that way, the articular interface between the glenoid component, which is secured to the glenoid, and the rest of the prosthesis is lateralized and lowered with respect to the scapula, which gives the possibility of increasing the lever arm of the deltoid. This reversed prosthesis is therefore particularly indicated when the cuff of the patient is highly damaged, or even torn, partially or completely. Moreover, the aforesaid articular interface has double mobility, in the sense that the glenohumeral component of the invention remains mobile both with respect to the glenoid, that fixedly bears the glenoid component, and with respect to the humerus, that bears no fixed prosthetic component: this double mobility between the glenoid and the humerus provides a greater range of motion between the glenoid and the humerus. Besides, as the shoulder prosthesis of the invention does not include a prosthetic humeral component, there is no need to secure any prosthetic component to the humerus, which avoids loosening of the securement of such a humeral component.

According to additional advantageous features of the glenohumeral component and of the shoulder prosthesis:
 the glenoid component comprises a glenosphere;
 the glenohumeral component is in one piece on which are defined both the convex and concave articular surfaces of the glenohumeral component;
 the glenohumeral component comprises a first piece, on which is defined the convex articular surface of the glenohumeral component, and a second piece, on which is defined the concave articular surface of the glenohumeral component, the first piece and the second piece being separate and being fixedly assembled together;
 the glenohumeral component comprises at least one third piece that is fixedly interposed between the first and second pieces;
 the convex articular surface of the glenohumeral component is defined on a ceramic part of the glenohumeral component;
 the convex articular surface of the glenohumeral component is defined on a metal part of the glenohumeral component;
 the concave articular surface of the glenohumeral component is defined on a polymeric part of the glenohumeral component, and the convex articular surface of the glenoid component is defined on a ceramic part of the glenoid component;
 the concave articular surface of the glenohumeral component is defined on a polymeric part of the glenohumeral component, and the convex articular surface of the glenoid component is defined on a metal part of the glenoid component;
 the concave articular surface of the glenohumeral component is defined on a ceramic part of the glenohumeral component, and the convex articular surface of the glenoid component is defined on a polymeric part of the glenoid component;
 the concave articular surface of the glenohumeral component is defined on a metal part of the glenohumeral component, and the convex articular surface of the glenoid component is defined on a polymeric part of the glenoid component;
 the concave articular surface of the glenohumeral component is defined on a ceramic part of the glenohumeral component, and the convex articular surface of the glenoid component is defined on a ceramic part of the glenoid component;

the ceramic part of the glenohumeral component and/or the ceramic part of the glenoid component are made of pyrocarbon;

the glenohumeral component includes a peripheral flange designed to abut against an edge of the end portion of the humerus, the edge bordering the bone surface, so as to limit range of articulation between the glenohumeral component and the humerus.

Embodiments of the invention will be better understood from reading the description which will follow, which is given solely by way of example and with reference to the drawings in which.

Figure 1:
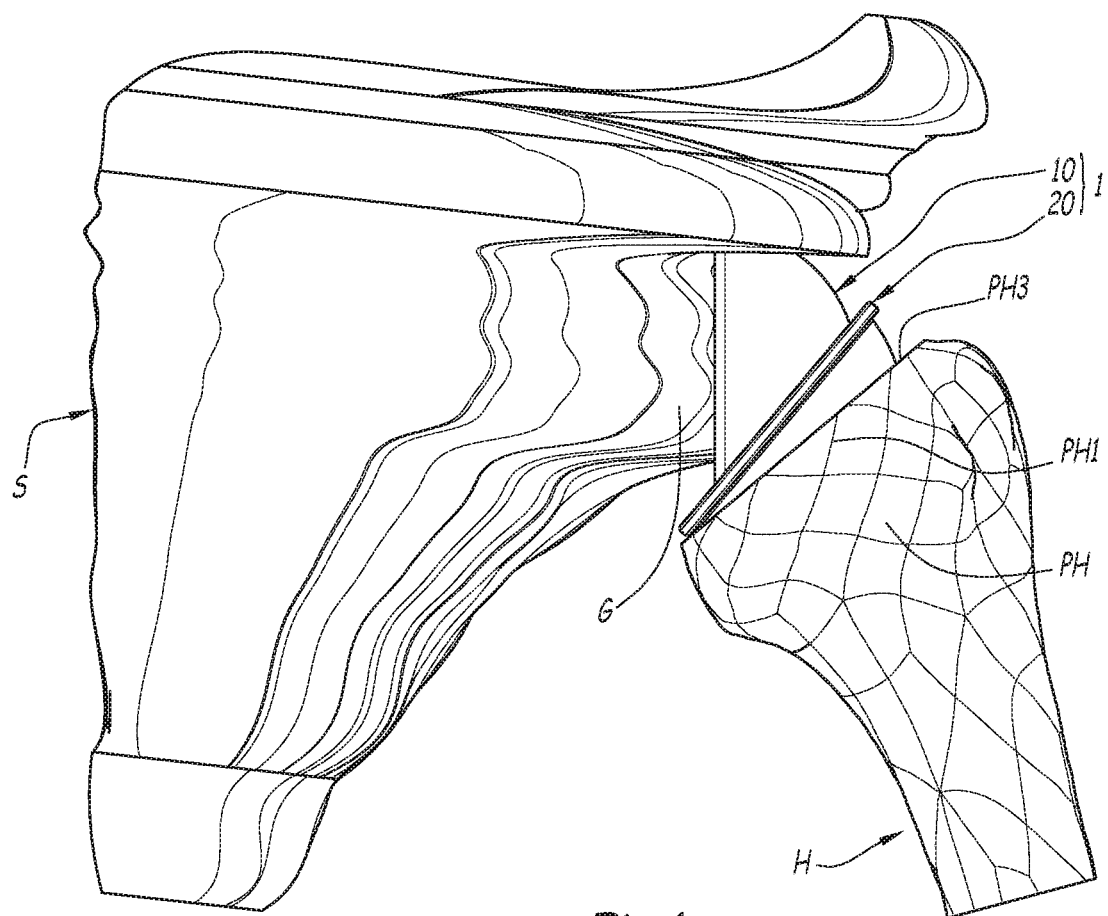
FIG. 1 is an elevational view of a shoulder prosthesis that is implanted at a human shoulder.
Figure 3:
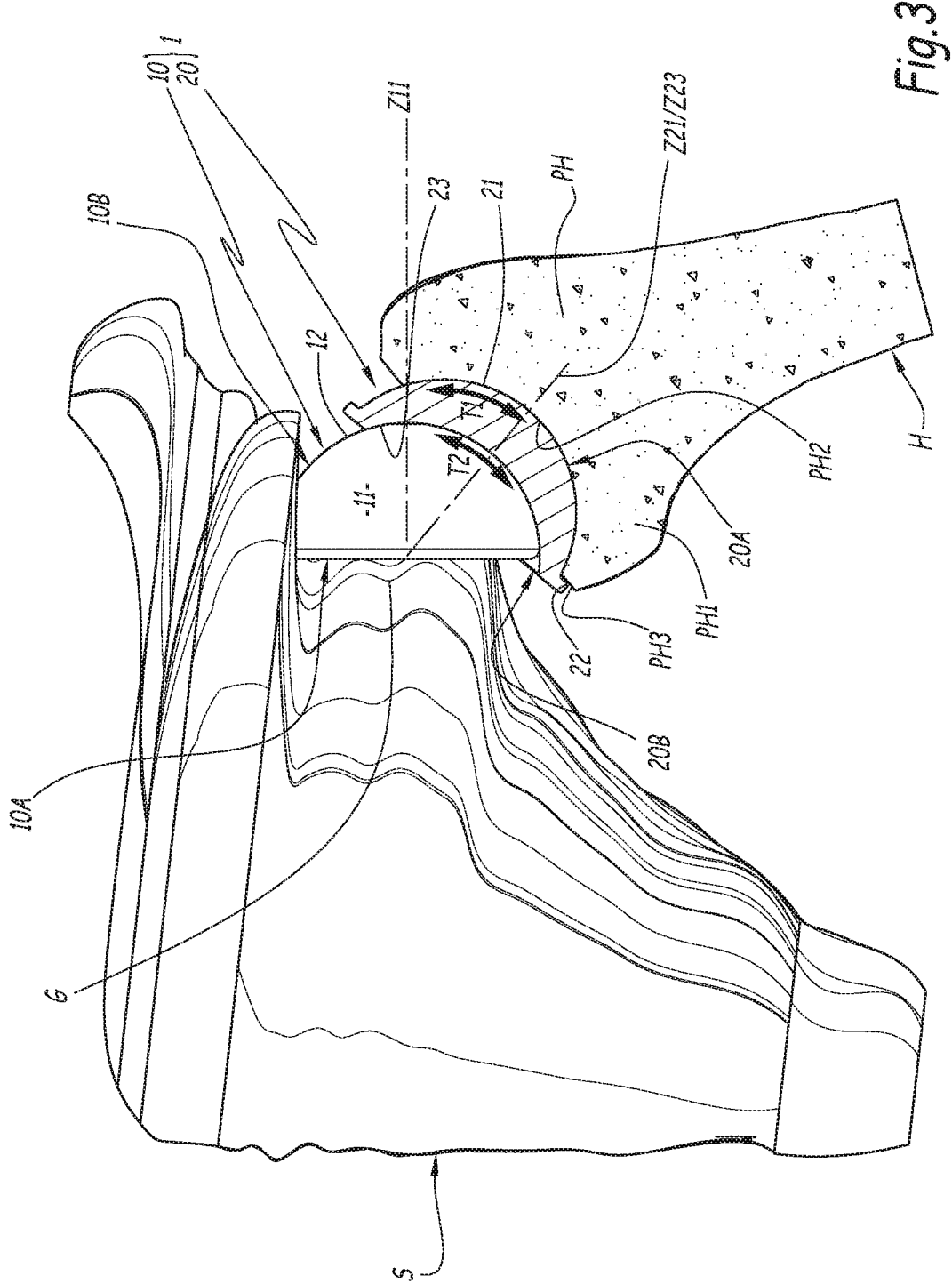
Figure 4:
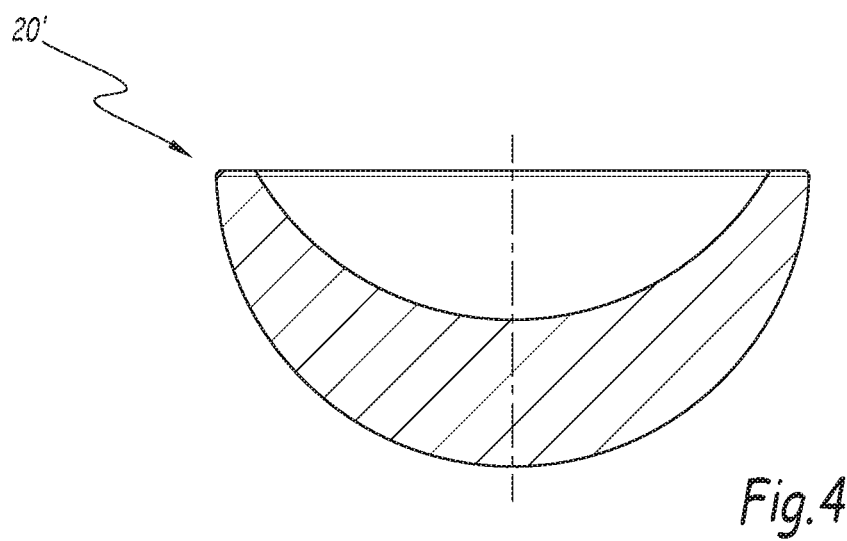
Figure 5:
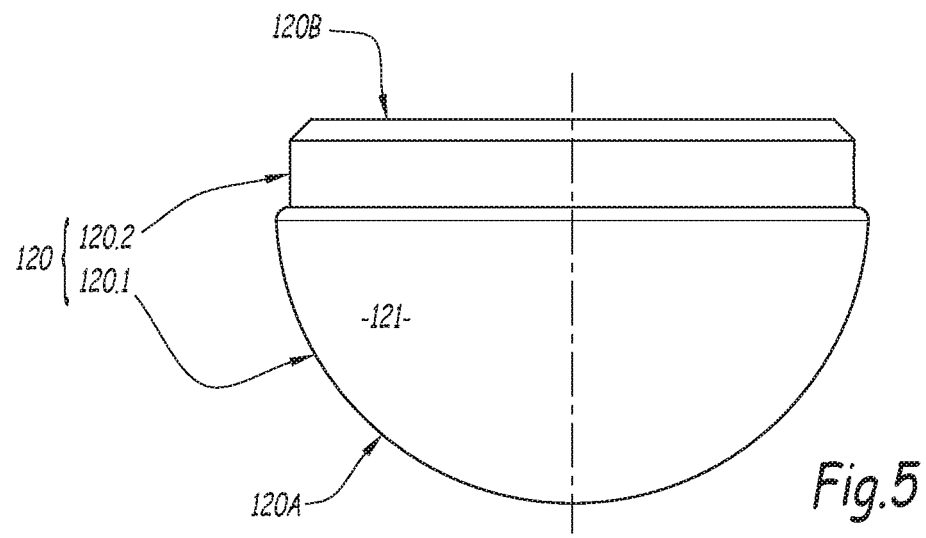
Figure 6:
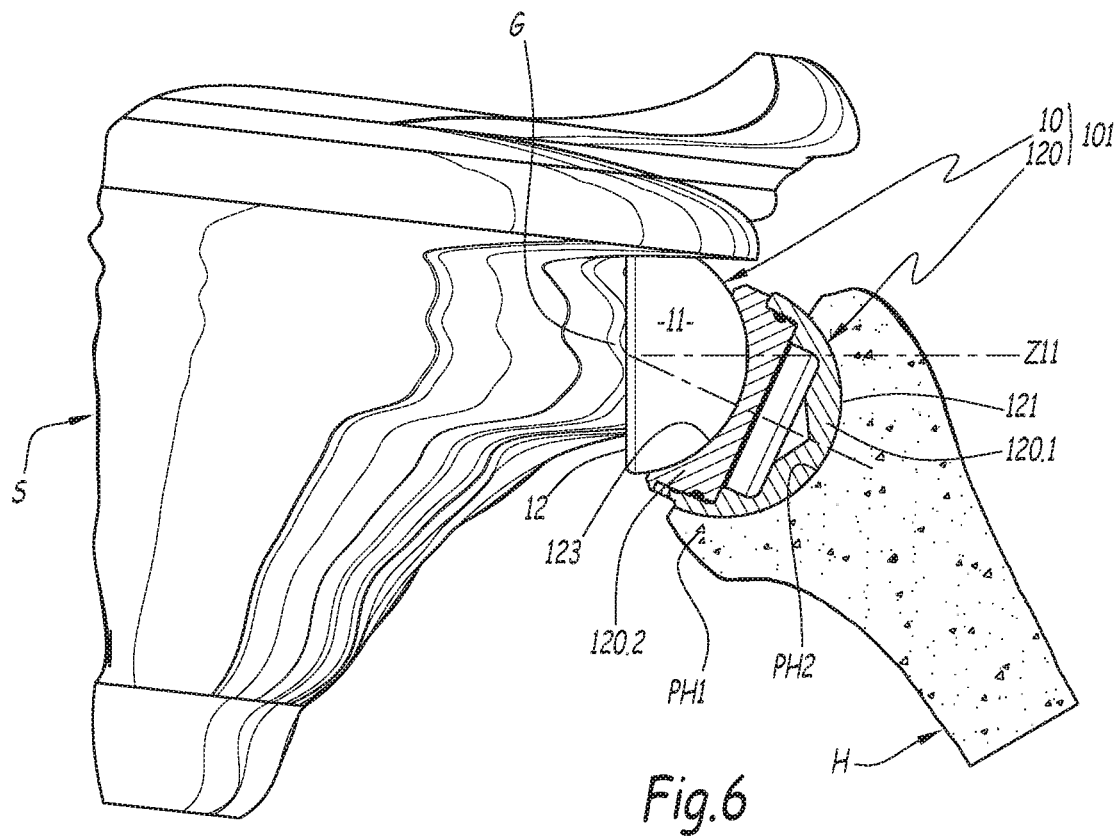

FIG. 3 corresponds to FIG. 1, in which the glenohumeral component and the humerus of the shoulder are illustrated in cross-section;

FIG. 4 is a cross-sectional view of a variant of the glenohumeral component of the shoulder prosthesis of FIG. 1;

FIG. 5 is an elevational view of another embodiment of a shoulder prosthesis;

FIG. 6 is a view similar to FIG. 3, with the shoulder prosthesis of FIG. 5; and

Figure 7:
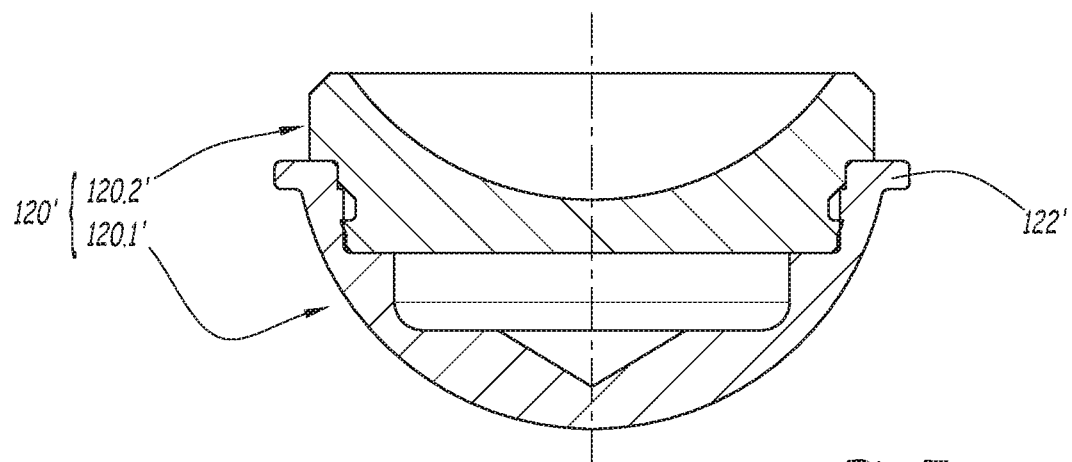

FIG. 7 is a cross-sectional view of a variant of the glenohumeral component of the shoulder prosthesis of FIG. 5.

The FIGS. 1 and 3 show a human shoulder at which a humerus H and a scapula S are associated. The FIGS. 1 and 3 also show a shoulder prosthesis 1 which is implanted at the aforesaid shoulder so as to join a glenoid G of the scapula and a proximal humerus PH of the humerus H in an articulated manner.

Figure 2:
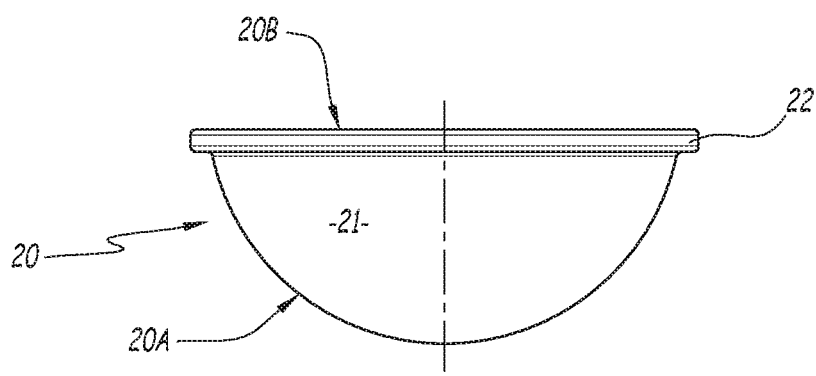
FIG. 2 is an elevational view of a glenohumeral component of the shoulder prosthesis of FIG. 1, this glenohumeral component being shown alone.

The shoulder prosthesis 1 comprises a glenoid component 10 and a glenohumeral component 20 that is shown alone in FIG. 2.

In some embodiments as the one shown in the figures, the shoulder prosthesis 1 consists of the glenoid component 10 and the glenohumeral component 20: in other words, the shoulder prosthesis 1 does not include any component other than the glenoid component 10 and the glenohumeral component 20.

The glenoid component 10 is designed to be secured to the glenoid G. For this purpose, the glenoid component 10 is provided with corresponding anchoring arrangements which are located at a side 10A of the glenoid component, which faces the glenoid G when the glenoid component is implanted. In practice, these anchoring arrangements of the glenoid component 10, which are not detailed in the figures, are known per se. More generally, the embodiments of the anchoring arrangements of the glenoid component 10 are not limitative, provided these anchoring arrangements are operable intraoperatively by a surgeon to fixedly fasten the glenoid component 10 to the glenoid G.

On a side 10B of the glenoid component 10, which is opposite to the side 10A, the glenoid component 10 has an articular surface 11, which is convex and which is provided to articulate with the glenohumeral component 20 as explained later.

In some embodiments as the one shown in the figures, the convex articular surface 11 is essentially spherical, being centered on an axis Z11, and is defined on a piece of the glenoid component 10, which forms a glenosphere 12.

In some embodiments, the glenosphere 12 or, more generally, the part of the glenoid component 10 on which the articular surface 11 is defined is made of a hard material, typically made of metal, especially surgical metal alloys, or ceramic, especially pyrocarbon. In some other embodiments, the glenosphere 12 or, more generally, the part of the glenoid component on which the articular surface 11 is defined is made of a soft material, typically made of polymeric material.

Unlike the glenoid component 10, the glenohumeral component 20 is not provided to be secured neither to the scapula S, especially the glenoid G thereof, nor to the humerus H, especially the proximal humerus PH thereof: as shown in the FIGS. 1 and 3, in the implanted state of the shoulder prosthesis 1, the glenohumeral component is free-floating with respect to the scapula S, especially the glenoid thereof, and with respect to the humerus H, especially the proximal humerus PH thereof. For this purpose, the glenohumeral component 20 is designed to be interposed in a freely movable manner between the proximal humerus PH and the glenoid component 10 secured to the glenoid G.

Thus, the glenohumeral component 20 has a side 20A, which faces the proximal humerus PH when the shoulder prosthesis 1 is implanted and which is in direct contact with an end portion PH1 of the proximal humerus PH. And the glenohumeral component 20 has a side 20B, which is opposite to the side 20A and which is in direct contact with the glenoid component 10 when the shoulder prosthesis 1 is implanted.

As shown by the FIGS. 2 and 3, the side 20A of the glenohumeral component 20 includes a convex articular surface 21 that is designed to articulate with a complementary concave bone surface PH2 of the end portion PH1 of the proximal humerus PH. If necessary after having partly resected the end portion PH1 of the proximal humerus PH, the bone surface PH2 is prepared within this end portion PH1 before putting in place the glenohumeral component 20 upon implantation of the shoulder prosthesis 1. The preparation and the constituent elements of the bone surface PH2 are not limitative, provided the bone surface PH2 is shaped as a recessed socket into the end portion PH1 of the proximal humerus PH and the bone surface PH2 is defined by osseous material, either natural or synthetic. Some embodiments of the bone surface PH2 are given for example in US 2011/0098822 that is incorporated therein by reference.

In some embodiments as the one shown in the FIGS. 1 to 3, the convex articular surface 21 is essentially spherical and is centered on an axis Z21.

When the shoulder prosthesis 1 is implanted, the convex articular surface 21 and the concave bone surface PH2 are in direct contact so as to freely articulate one with respect to the other, especially somewhat in the manner of a ball joint. Thus, the convex articular surface 21 and the concave bone surface PH2 freely tilt one with respect to one another both in the cross-sectional plane of FIG. 3, as indicated by an arrow T1 on FIG. 3, and in all the other geometric planes containing a central geometrical axis of the bone surface PH2.

In some embodiments as the one shown in the FIGS. 1 to 3, the articulation between the glenohumeral component 20 and the proximal humerus H, which results from the above-described cooperation between the convex articular surface 21 and the concave bone surface PH2, has a range which may be limited, especially in order to prevent any unwanted disengagement between the articular surface 21 and the bone surface PH2. For this purpose, the side 20A of the glenohumeral component 20 is provided with a peripheral flange 22 which is designed to abut against the end portion PH1 of the proximal humerus PH, more precisely to abut against an edge PH3 of this end portion PH1, which borders the concave bone surface PH2. As shown for example for the articulation configuration of FIG. 3, this flange 22 mechanically interferes with a lower portion of the edge PH3 so as to limit the range of tilting between the glenohumeral component 20 and the proximal humerus PH in the cross-sectional plane of FIG. 3.

As shown by the FIG. 3, the side 20B of the glenohumeral component 20 includes a concave articular surface 23 that is complementary to the convex articular surface 11 of the glenoid component 10 and that is thus designed to articulate with this articular surface 11 when the shoulder prosthesis 1 is implanted.

In some embodiments as the one shown in the FIGS. 1 to 3, the concave articular surface 23 is essentially spherical and is centered on an axis Z23 which may be coincident with the axis Z21 of the convex articular surface 21.

When the shoulder prosthesis 1 is implanted, the concave articular surface 23 of the glenohumeral component 20 and the convex articular surface 11 of the glenoid component 10 are in direct contact so as to freely articulate one with respect to the other, especially somewhat in the manner of a ball joint. In some embodiments as the one shown in the FIGS. 1 to 3, the type of articulation between the articular surfaces 11 and 23 is similar or even identical to the type of articulation between the articular surface 21 and the bone surface PH2. Thus, the articular surface 11 and 23 freely tilt one with respect to the other both in the cross-sectional plane of FIG. 3, as indicated by an arrow T2 on FIG. 3, and in all the other geometric planes containing a central geometric axis of the articular surface 11, especially the axis Z11.

It will be understood that in use, a double mobility is operable between the glenoid component 10, that is fixedly fastened to the glenoid G, and the proximal humerus PH: a first mobility is operated by cooperation between the articular surface 21 and the bone surface PH2 and a second mobility is operated by cooperation between the articular surfaces 11 and 23. According to the various movements of the shoulder provided with the shoulder prosthesis 1, one and/or the other of these first and second mobilities are more or less implemented, which provides a greater range of motion between the glenoid G and the proximal humerus PH. Furthermore, thanks to the fact that the opposed articular surfaces 21 and 23 of the glenohumeral component 20 have respective curvatures that are opposite, the aforesaid double mobility remains stable in use, with the advantage that the concavity of the articular surface 23 enables to combine the glenohumeral component 20 with a reversed glenoid component as the glenoid component 10, in the sense that unlike a natural glenoid, the glenoid G provided with the glenoid component 10 has a convex shape at the articular surface 11: compared to a natural glenoid, the articulation between the glenoid G, provided with the glenoid component 10, and the glenohumeral component 20 is lateralized and lowered with respect to the scapula S. In this regard, the shoulder prosthesis 1 can be considered as a reversed shoulder prosthesis with all the corresponding functional advantages. That being said, the reversed shoulder prosthesis 1 has, as a specific aspect, no prosthetic humeral component which would be fixedly fastened to the proximal humerus PH, since the glenohumeral component 20 remains free-floating with respect to the proximal humerus P: there is no need to secure any such prosthetic component to the humerus H, which avoids the risk that such a prosthetic component separates from the humerus in an uncontrolled manner as a result of high loads transmitted therethrough to the humerus.

In some embodiments as the one shown in the FIGS. 1 to 3, the glenohumeral component 20 is made in one piece on which both articular surfaces 21 and 23 are defined.

It follows that this one-piece glenohumeral component 20 is preferably made of a hard material, typically made of metal, especially surgical metal alloys, or ceramic, especially pyrocarbon: such a hard material provides a good articular behavior with respect to the osseous material of the bone surface PH2 of the proximal humerus PH. In that case, the glenosphere 12 or, more generally, the part of the glenoid component 10 on which the articular surface 11 is defined may advantageously be made of a soft material, typically polymeric material. That being said, in some embodiments, both components 20 and 10 may be each made of a hard material, ceramic and ceramic for example.

Alternatively, the one-piece glenohumeral component 20 is made of a soft material, typically polymeric material; in that case, the glenosphere 12 or, more generally, the part of the glenoid component 10 on which the articular surface 11 is defined is made of a hard material, typically metal, especially surgical metal alloys, or ceramic, especially pyrocarbon.

Turning now to the FIG. 4, a variant of the glenohumeral component 20 is considered, being labelled 20'. This glenohumeral component 20' is identical to the glenohumeral component 20 of the FIGS. 1 to 3, except that the glenohumeral component 20' does not have a flange similar to the flange 22.

Turning now to the FIGS. 5 and 6, a shoulder prosthesis 101 is considered as an alternative embodiment for the shoulder prosthesis 1 of the FIGS. 1 to 3. The shoulder prosthesis 101 comprises or even consists of both a glenoid component, which is identical to the glenoid component 10 of the shoulder prosthesis 1 and which is therefore labelled 10 for the shoulder prosthesis 101, and a glenohumeral component 120. With respect to the proximal humerus PH and the glenoid component 10, the glenohumeral component 120 is functionally similar to the glenohumeral component 20: thus, two opposed sides 120A and 120B of the glenohumeral component 120 respectively include a convex articular surface 121 for articulating with the bone surface PH2 prepared within the end portion PH1 of the proximal humerus PH and a concave articular surface 123 for articulating with the articular surface 11 of the glenoid component, while having the glenohumeral component 120 that is free-floating with respect to the humerus H and the scapula S.

The glenohumeral component 120 differs from the glenohumeral component 20 by its constitutive structure, in the sense that unlike being made in one piece, the glenohumeral component 120 comprises two distinct pieces 120.1 and 120.2. The piece 120.1 defines the convex articular surface 121 whereas the piece 120.2 defines the concave articular surface 123. In use, the two separate pieces 120.1 and 120.2 are fixedly assembled together. In practice, the means for fixedly assembling the pieces 120.1 and 120.2 are not limitative, any appropriate embodiment, known per se, being possible for these means.

The two pieces structure of the glenohumeral component 120 may advantageously use to provide two different materials for the pieces 120.1 and 120.2 respectively. Thus, in some embodiments, the piece 120.1 may be made of a hard material, typically made of metal, especially surgical metal alloys, or ceramic, especially pyrocarbon, whereas the piece 120.2 may be made of a soft material, typically made of polymeric material, being noted that in that case, the glenosphere 12 or, more generally, the part of the glenoid component 10 on which the articular surface 11 is defined is preferably made of a hard material, typically made of metal or ceramic.

Alternatively, the piece 120.1 may be made of a soft material whereas the piece 120.2 may be made of a hard material.

In some embodiments as the one shown in the FIGS. 5 and 6, the glenohumeral component 120 consists of the two pieces 120.1 and 120.2 and, if appropriate, added elements of the aforesaid means for assembling these two pieces together. That being said, in some other embodiments, the glenohumeral component may include at least one third piece that is distinct from the two pieces 120.1 and 120.2: this third piece is fixedly interposed between the pieces 120.1 and 120.2, which may facilitate the combination of the pieces 120.1 and 120.2 when these latter are difficult to directly assemble together.

Turning now to the FIG. 7, a variant for the glenohumeral component 120 is considered, being labelled 120'. The glenohumeral component 120' is identical to the glenohumeral component 120 of the FIGS. 5 and 6, except that the glenohumeral component 120' is provided with a peripheral flange 122' which is functionally similar to the flange 22 of the glenohumeral component 20.

In some embodiments, as the one shown in the FIG. 7, the flange 122' belongs to a piece 120.1' of the glenohumeral component 120', which is similar to the piece 120.1. In some other embodiments, a piece 120.2' of the glenohumeral component 120', which is similar to the piece 120.2, includes the flange 122'.

The invention claimed is:

1. A method of implanting a reversed shoulder prosthesis, the method comprising:
    securing a glenoid component having a convex articular surface to a human glenoid;
    resecting a portion of a proximal end of a humerus of a human shoulder, thereby forming a resected bone surface;
    preparing the resected bone surface such that the resected bone surface comprises a concave bone surface;
    interposing a glenohumeral component between the glenoid component and the resected bone surface such that a concave articular surface of the glenohumeral component is placed in direct contact with and freely articulates with the convex articular surface of the glenoid component and a convex articular surface of the glenohumeral component is placed in direct contact with and freely articulates with the concave bone surface;
    wherein the interposed glenohumeral component remains free-floating with respect to both the proximal end of the humerus and the glenoid component.

2. The method of claim 1, wherein interposing the glenohumeral component comprises positioning a peripheral flange of the glenohumeral component adjacent to a portion of the resected bone surface such that a side of the peripheral flange facing the resected bone surface contacts the resected bone surface at a limit of a range of articulation of the glenohumeral component relative to the proximal end of the humerus.

3. The method of claim 2, wherein one piece of the glenohumeral component includes both the peripheral flange and the entirety of the convex articular surface of the glenohumeral component.

4. The method of claim 2, wherein an external angle along the convex articular surface of the glenohumeral component between opposed portions of the peripheral flange is 180 degrees.

5. The method of claim 1, wherein the method does not include securing any prosthetic articular component to the humerus.

6. The method of claim 1, wherein the glenoid component comprises a glenosphere.

* * * * *